(12) United States Patent
Brammer

(10) Patent No.: US 10,753,780 B2
(45) Date of Patent: Aug. 25, 2020

(54) LIQUID DISPERSER

(71) Applicant: David Allan Brammer, Smyrna, GA (US)

(72) Inventor: David Allan Brammer, Smyrna, GA (US)

( * ) Notice: Subject to any disclaimer, the term of this patent is extended or adjusted under 35 U.S.C. 154(b) by 2 days.

(21) Appl. No.: 16/298,220

(22) Filed: Mar. 11, 2019

(65) Prior Publication Data

US 2019/0301914 A1 Oct. 3, 2019

Related U.S. Application Data

(60) Provisional application No. 62/641,861, filed on Mar. 12, 2018.

(51) Int. Cl.
*G01F 11/02* (2006.01)

(52) U.S. Cl.
CPC .................... *G01F 11/027* (2013.01)

(58) Field of Classification Search
CPC ............................................. G01F 11/027
USPC ............................................................ 222/39
See application file for complete search history.

(56) References Cited

U.S. PATENT DOCUMENTS

| 6,854,620 | B2* | 2/2005 | Ramey | A61M 5/1456 |
| | | | | 222/153.13 |
| 2007/0145077 | A1* | 6/2007 | Harrold | B05B 11/3015 |
| | | | | 222/256 |
| 2009/0050140 | A1* | 2/2009 | Patel | A61M 15/0045 |
| | | | | 128/200.18 |
| 2010/0011889 | A1* | 1/2010 | Lemmo | B01L 9/56 |
| | | | | 73/864.34 |
| 2015/0314070 | A1* | 11/2015 | Heintz | C06D 5/10 |
| | | | | 222/1 |

OTHER PUBLICATIONS https://www.premierdentalco.com/product/prosthetic/traxodenti, Date unknown.

(Continued)

*Primary Examiner* — Jeremy Carroll

(57) ABSTRACT

A dispenser for dispensing a metered amount of a liquid comprises a body having sidewalls defining a hollow interior and an opening at a forward end of the body, a cartridge having a reservoir adapted to contain a liquid and an outlet at the forward end of the cartridge, the cartridge being sized and shaped to be positioned in the hollow interior of the body so that the outlet is aligned with the opening in the body. A plunger is positionable in the reservoir and slidable within the reservoir, and a metering unit comprises a plunger advancement mechanism that can cause the plunger to slide within the reservoir, the metering unit causing the plunger advancement mechanism to advance the plunger a predetermined amount. The metering unit is configured to cause advancement the plunger in the reservoir to apply pressure on the liquid in the reservoir and cause a droplet of the liquid to be dispensed through the outlet. The dispenser produces a droplet of from about 0.5 μl to about 10.0 μl. In one version, a droplet to droplet consistency of ±0.2 μl. In one version, the metering unit provides feedback to a user when the plunger has been advanced the predetermined distance.

19 Claims, 5 Drawing Sheets

(56) References Cited

OTHER PUBLICATIONS https://www.optimusdentalsupply.com/profil-c3-syringe-4gm-hybrid-cornposite-ea/, Date unknown.
https://gentec-benelux.com/product-details/precidot-manual-dosing-tool/, Date unknown.
https://www.net32.com/ec/mark-iiip-centrix-autoclavable-plastic-dispense/ Date unknown.
https://www.crpump.com/a/Syringe_pump/ZS100/20170424/60.html, Date unknown.
https://www.dispensinglink.com/store/p15/8880370PKG_%3D_30CC_Plastic_Manual_Syringe_Gun_Package.html, Date unknown.
http://www.vedefar.com/en/detail_28.aspx, Date unknown.
https://www.intertronics.co.uk/product/preeflow-eco-pen-precision-volumetric-dosing-pump/, Date unknown.
http://en.bonkote.co.jp/product/peripherals/bonpen.html, Date unknown.
https://www.hamiltoncompany.com/laboratory-products/syringes/syringe-accessories/pb600-repeating-dispenser, Date unknown.
German et al., "Reliability of drop size from multi-dose eye drop bottles: is it cause for concern?" Eye, 13, 93-100, 1999 Royal College of Opthalmologists.
https://www.drugs.com/cg/insulin-pens.html, date unknown.
https://www.renewcbdstore.com/, date unknown.
https://www.supplyclinic.com/items/rc-prep-microdose-intro-kit/ Date unknown.
https://esyringe.com/1ml-high-pressure-bevel.aspx, Date unknown.
https://www.dentalwarehouse.co.za/shop/endodontics/endodontics-miscellaneous-endodontics/root-canal-pressure-syringe/, Date unknown.
https://www.vlowmedical.com/, Date unknown.
http://vp-sci.com/vp-121-1.html, Date unknown.
https://www.neogen.com/neocenter/press-releases/neogen-launches-prima-shot-repeater-syringe, Date unknown.
https://www.atozvetsupply.com/Parts-for-Allflex-50ml-Repeater-50MR2-Syringe-p/761-50mr2parts.htm, Date unknown.

\* cited by examiner

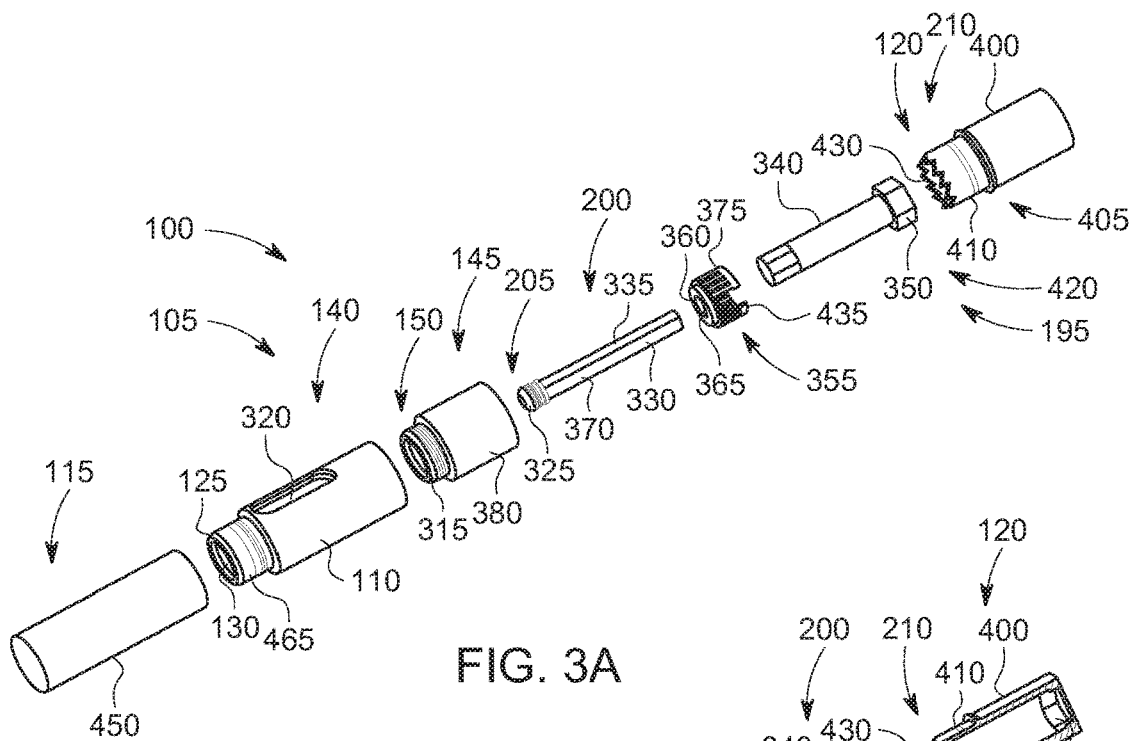

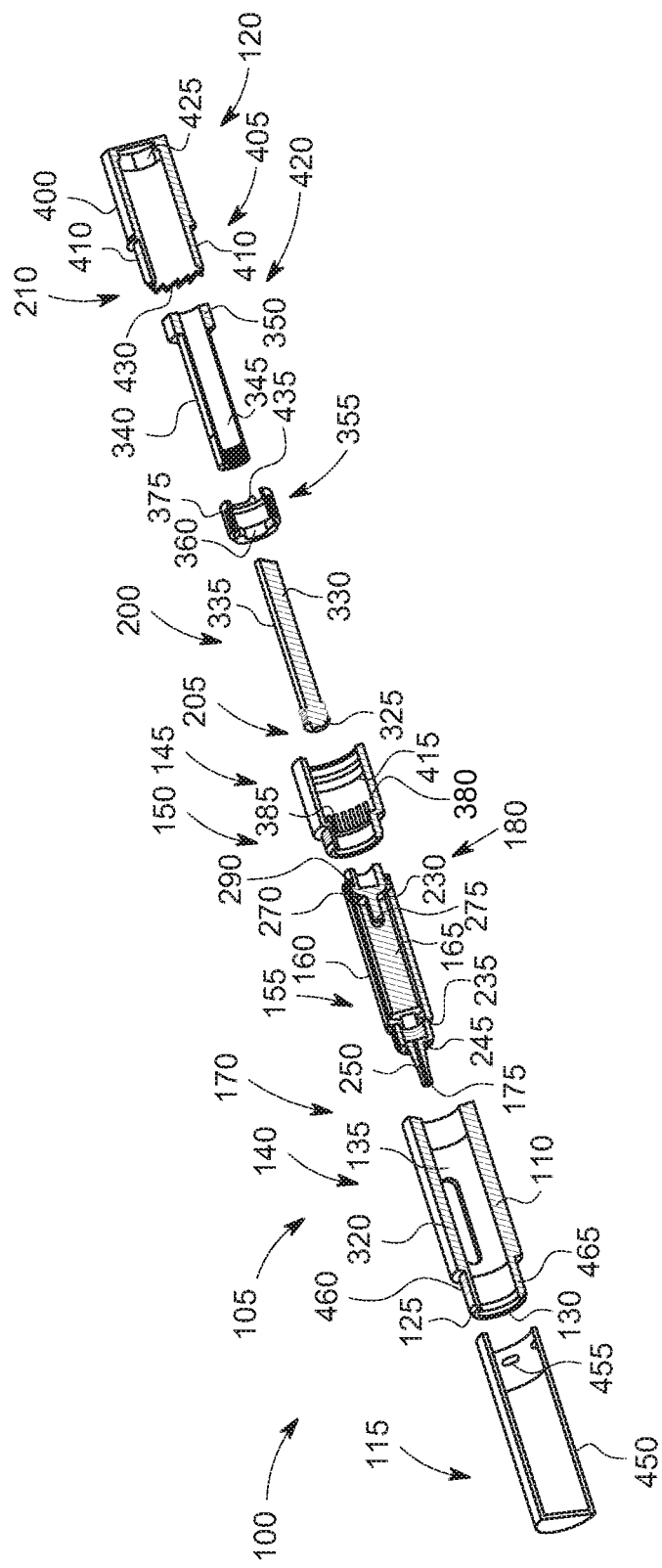
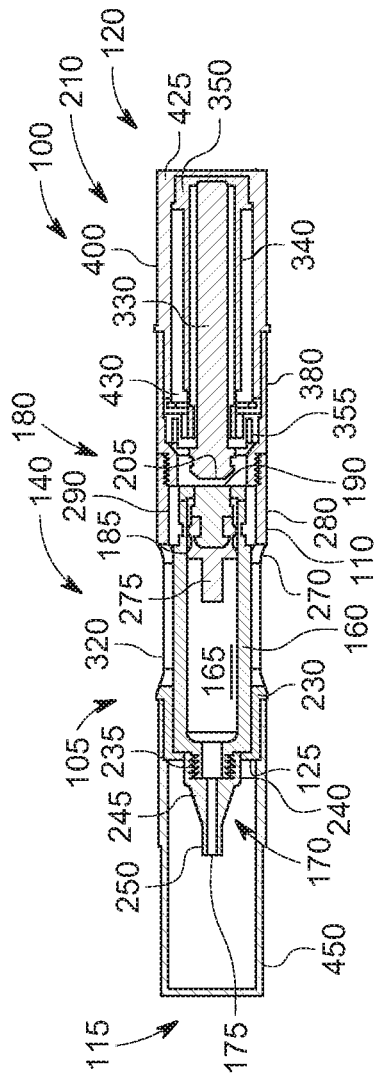
FIG. 4A
FIG. 4B

LIQUID DISPERSER

PRIORITY

The present application claims the benefit of domestic priority based on U.S. Provisional Patent Application 62/641,861 filed on Mar. 12, 2018, the entirety of which is incorporated herein by reference.

BACKGROUND

Liquid dispensers are used for a variety of purposes. Of particular interest are liquid droplet dispensers. Liquid droplet dispensers can generate a small amount of a liquid substance for administration to a user or for addition to another substance.

For example, droplets containing an active ingredient, such as a pharmaceutical agent, a vitamin, an essential oil, or the like can be administered to a user directly or by addition to a formulation that is later administered to the user. The droplet and/or formulation can be administered orally, topically, inhaled as a vapor, and/or in numerous other manners. The droplet often contains one or more ingredients that are expensive and/or that need to be precisely metered for effectiveness and safety. Thus, it is important to be able to reproducibly generate a consistent sized droplet.

An increasingly popular way to administer a liquid in aerosolized form to a user is through a vaporizer or a vaping tool. A droplet of liquid, often an oil, is vaporized and delivered to the user during the user's inhalation. However, current liquid dispensers for vaporizers and vaping tools suffer from several drawbacks. For example, dispensers lack convenience, consistency, precision, and/or feedback.

There is therefore a need for an improved liquid dispenser. There is further a need for a liquid dispenser that can produce a metered droplet. There is still a further need for a dispenser that is convenient, consistent, precise, and that provides feedback to the user.

SUMMARY

The present invention satisfies these needs. In one aspect of the invention, an improved liquid dispenser is provided.

In another aspect of the invention, a liquid dispenser is provided that produces metered droplets.

In another aspect of the invention, a liquid dispenser is provided that produces consistent and reproducible droplets.

In another aspect of the invention, a liquid dispenser is provided that is convenient to use and to store.

In another aspect of the invention, a liquid dispenser provides a feedback to a user when a metered droplet has been produced.

In another aspect of the invention, a dispenser for dispensing a metered amount of a liquid comprises a body having sidewalls defining a hollow interior and an opening at a forward end of the body, a cartridge having a reservoir adapted to contain a liquid and an outlet at the forward end of the cartridge, the cartridge being sized and shaped to be positioned in the hollow interior of the body so that the outlet is aligned with the opening in the body, a plunger positionable in the reservoir and slidable within the reservoir, and a metering unit comprising a plunger advancement mechanism that can cause the plunger to slide within the reservoir, the metering unit causing the plunger advancement mechanism to advance the plunger a predetermined amount, wherein the metering unit is configured to cause advancement the plunger in the reservoir to apply pressure on the liquid in the reservoir and cause a droplet of the liquid to be dispensed through the outlet, and wherein the dispenser produces a droplet of from about 0.5 µl to about 10.0 µl with a droplet to droplet consistency of ±0.2 µl.

In another aspect of the invention, a dispenser for dispensing a metered amount of a liquid comprises a body having sidewalls defining a hollow interior and an opening at a forward end of the body, a cartridge having a reservoir adapted to contain a liquid and an outlet at the forward end of the cartridge, the cartridge being sized and shaped to be positioned in the hollow interior of the body so that the outlet is aligned with the opening in the body, a plunger positionable in the reservoir and slidable within the reservoir, and a metering unit comprising a plunger advancement mechanism that can cause the plunger to slide within the reservoir, the metering unit causing the plunger advancement mechanism to advance the plunger a predetermined amount, wherein the metering unit is configured to cause advancement the plunger a predetermined distance in the reservoir to apply pressure on the liquid in the reservoir and cause a droplet of the liquid of from about 0.5 µl to about 10.0 µl to be dispensed through the outlet, and wherein the metering unit provides feedback to a user when the plunger has been advanced the predetermined distance.

In another aspect of the invention, a method of dispensing a droplet of liquid comprises providing a dispenser comprising a body having sidewalls defining a hollow interior and an opening at a forward end of the body, a cartridge having a reservoir adapted to contain a liquid and an outlet at the forward end of the cartridge, the cartridge being sized and shaped to be positioned in the hollow interior of the body so that the outlet is aligned with the opening in the body, a plunger positionable in the reservoir and slidable within the reservoir, and a metering unit comprising a plunger advancement mechanism that can cause the plunger to slide within the reservoir, the metering unit causing the plunger advancement mechanism to advance the plunger a predetermined amount, actuating the metering unit to dispense a discrete, accurate, and reproducible droplet of liquid of from about 0.5 µl to about 10.0 µl from the outlet, and administering the droplet.

DRAWINGS

These features, aspects, and advantages of the present invention will become better understood with regard to the following description, appended claims, and accompanying drawings which illustrate exemplary features of the invention. However, it is to be understood that each of the features can be used in the invention in general, not merely in the context of the particular drawings, and the invention includes any combination of these features, where:

FIG. 3A is a schematic perspective exploded view of a dispenser according to a version of the invention;

FIG. 3B is a schematic perspective sectional exploded view of the dispenser of FIG. 3A;

FIG. 3C is a schematic perspective view of the assembled dispenser of FIG. 3A;

FIG. 4A is a schematic perspective exploded view of the dispenser of FIG. 3A with a cartridge;

FIG. 4B is a schematic sectional view of the assembled dispenser of FIG. 4A;

DESCRIPTION

The present invention relates to a liquid dispenser. In particular, the invention relates to a liquid dispenser for producing a droplet of liquid. Although the liquid dispenser is illustrated and described in the context of being useful for generating precisely metered droplets, the present invention can be useful in other instances. Accordingly, the present invention is not intended to be limited to the examples and embodiments described herein.

Figure 1A:
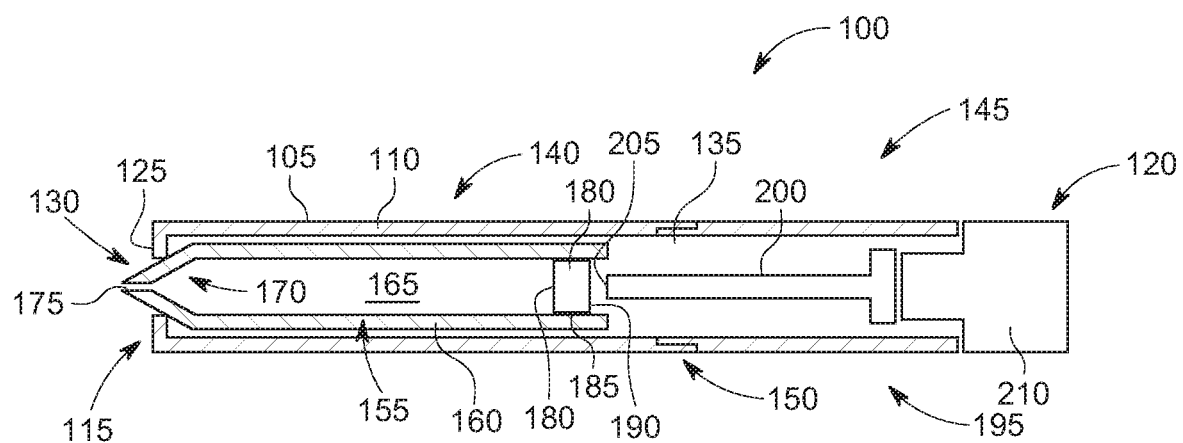
FIG. 1A is a schematic sectional side view of a dispenser according to the invention.

FIG. 1A illustrates a dispenser 100 according to the invention. The dispenser 100 includes an outer body 105 comprising a sidewall 110 which may be cylindrical in shape, a front end 115, and a rear end 120. The front end 115 includes an annular lip 125 that defines an opening 130 positioned along a central longitudinal axis of the body 105. Within the sidewall 110 is a hollow interior 135 of the body 105. The body 105 is optionally composed of two sections, a front section 140 and a rear section 145 that are connected to one another at a connector 150 that allows for selective disconnection of the front section 140 from the rear section 145. When the connector 150 is disconnected, access can be gained to the interior 135 of the body 105. The connector 150 can be, for example, a threaded connection, a bayonet connection, a press fit connection, or the like.

A cartridge 155 is receivable within the interior 135 of the body 105. The cartridge 155 includes a cylindrical wall 160 that defines within it a reservoir 165. The reservoir 165 can be filled with a liquid that is to be dispensed. At a forward end of the cartridge 155 is a tip 170 with an outlet 175 in fluid communication with the reservoir 165. The cylindrical wall 160 of the cartridge 155 is sized so that the cartridge can be slidable within the interior 135 of the body 105. Accordingly, the diameter of the cylindrical wall 160 of the cartridge 155 is sufficiently less than the inner diameter of the sidewall 110 of the body 105 to allow the cartridge 155 to slide in the body 105 but sufficiently large that the central longitudinal axis of the cartridge 155 generally aligns with the central longitudinal axis of the body 105. The diameter of the cylindrical wall 160 of the cartridge 155 is also larger than the opening 130 at the front end 115 of the body 105 so the cartridge 155 does not slide through the opening 130. The tip 170 of the cartridge tapers or steps down to a diameter smaller than the size of the opening 130 so that the outlet 175 can extend through the opening 130. A front surface of the tip 170 engages the inner edge of the opening 130 to prevent forward movement of the cartridge 155 within the interior 135 of the body 105. The opening 175 is sized so that liquid in the reservoir 165 does not readily flow through the opening 175 unless pressurized.

The size of the opening 175 can vary depending on the viscosity of the liquid in the reservoir 165. Higher viscosity liquids will have a larger opening that lower viscosity openings. In one version, the opening has a diameter of from about 0.4 mm to about 2.0 mm. In one version designed for use with higher viscosity liquids, the opening 175 has a diameter from about 0.8 mm to about 1.2 mm, more preferably about 1.0 mm. In another version designed for use with lower viscosity liquids, the opening 175 has a diameter from about 0.4 mm to about 0.8 mm, more preferably about 0.6 mm.

Within the reservoir 165 of the cartridge 155 is a plunger 180. The plunger 180 has a cylindrical outer surface 185 that sealingly engages the inner wall of the cartridge cylindrical wall 160 so that liquid contained within the reservoir 165 does not pass through or around the plunger 180. The plunger 180 is also slidable within the cartridge 155 when a sufficient forwardly directed force is applied thereto. Forward movement of the plunger 185 thus applies pressure to liquid within the reservoir 165 and causes liquid to flow out of the outlet 175 of the cartridge 155. The rear end of the cartridge 155 is open to allow access to the rear surface 190 of the plunger 180.

Also provided in the interior 135 of the body 105 is a plunger advancement mechanism 195 comprising a plunger contacting member 200 including a forward end 205 adapted to contact the rear surface 190 of the plunger 180. The plunger contacting member 200 is sufficiently small to be insertable inside the cartridge 155 and sufficiently long that it can push the plunger 180 towards the forward end of the cartridge 155. The plunger advancing mechanism 195 also comprises a metering unit 210 in communication with the plunger contact member 200 and capable of advancing the plunger contact member 200 a predetermined amount so that the plunger 180 is advanced a predetermined amount within the reservoir 165. As a result, a metered amount of liquid is dispensed from the outlet 175. The metering unit 210 can advance the plunger contacting member 200 and the plunger 180 the predetermined amount in response to actuation. In one version, the actuation is manual actuation and the metering unit 210 includes a mechanism to convert the manual actuation into the forward movement of the plunger contacting member 200.

Figure 1B:
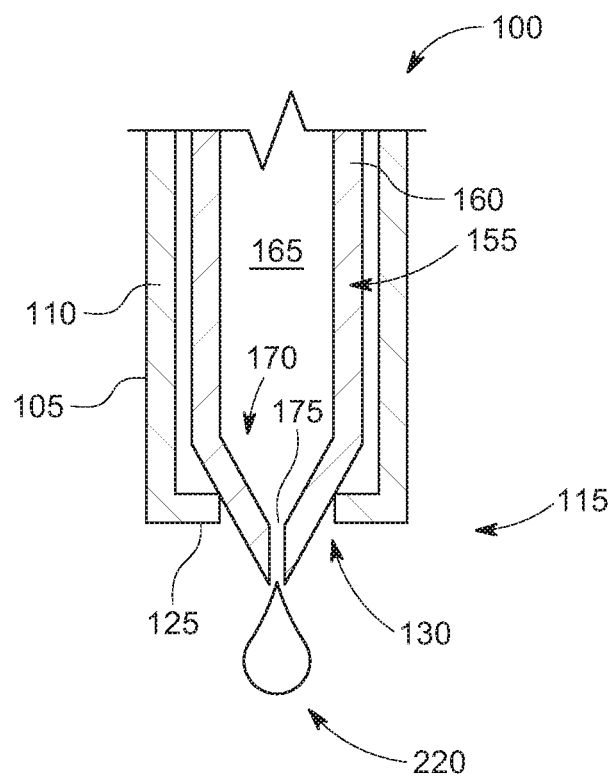
FIG. 1B is a schematic sectional side view showing the dispenser of FIG. 1A in use.

The dispenser 100 of FIG. 1A is particularly useful in providing a metered amount of a small quantity of liquid in a consistent and convenient manner. When the metering unit 210 is actuated, a droplet 220 of liquid from the reservoir 165 is dispensed, as shown in FIG. 1B. The dispenser 100 is particularly useful when precisely metered and/or highly accurate amounts of droplet sized quantities of costly liquids are desired. For example, the dispenser 100 can be used to dispense pharmaceutical formulations, therapeutic oils, essential oils, nutraceuticals, vitamin concentrates, cosmetics, adhesives, super glue, and the like. The liquid to be dispensed may be stored in a cartridge 155. When a droplet 220 of the liquid is needed, the cartridge 155 can be inserted into the interior 135 of the body 110. The plunger advancement mechanism 195 is actuated and the plunger 180 is moved forward a sufficient amount to cause the droplet 220 of a discrete amount of the liquid to exit the outlet 175.

The volume of the droplet 220 can be predetermined and can depend on the specific application and need. For example, the predetermined volume can range from about 0.5 microliters (µl) to about 10.0 µl, more preferably from about 0.7 µl to about 5.0 µl, more preferably from about 1.0 µl to about 2.5 µl, more preferably from about 1.5 µl to about 2 µl. In one particular version, the dispenser 100 produces a droplet having a volume of about 1.7 µl. In many applications, it is important to obtain droplet-to-droplet consistency. Accordingly, in one version, the dispenser 100 is designed to provide unexpectedly high droplet-to-droplet consistency. The droplet-to-droplet consistency of this version is ±0.5 µl, more preferably ±0.2 µl, more preferably ±0.1 µl. In one particular version, the dispenser 100 produces droplets of 1.7 µl with a standard deviation of 0.1 µl. Droplets above and below the above stated ranges can also be provided by adjusting the dispenser 100, as discussed in more detail below. The small droplet size and the reproducibility of the droplet size are each an advantageous advancement over the state of the art. Conventional droppers produce a range of drops from 33.8 µl to 63.4 µl, depending on the manufacturer, with a variability of ±2.2 µl to ±10.8 µl (Emma J. German et al "Reliability of drop size from multi-dose eye drop bottles: is it cause for concern?" nature.com/articles/eye199917.pdf).

Figure 2A:
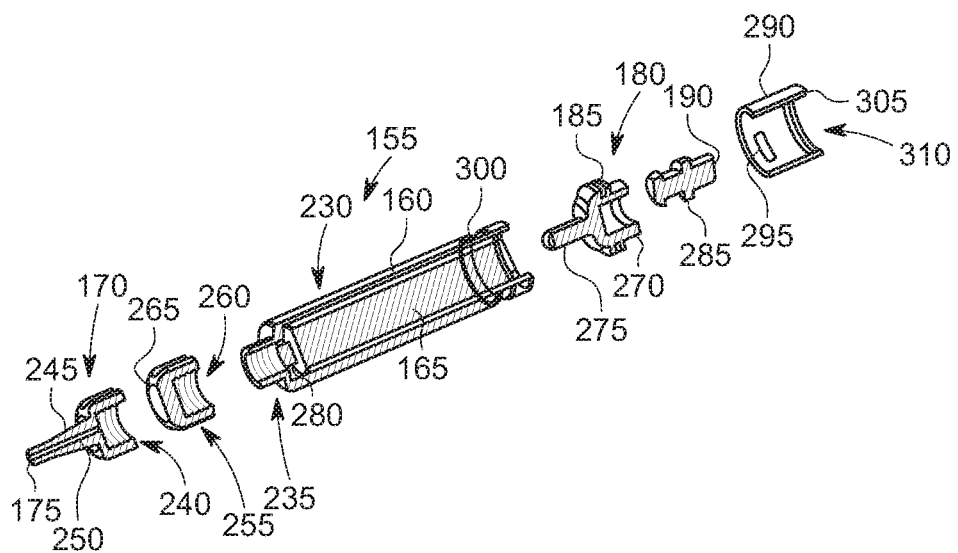
FIG. 2A is a schematic perspective exploded view of a cartridge of the dispenser of FIG. 1A.
Figure 2B:
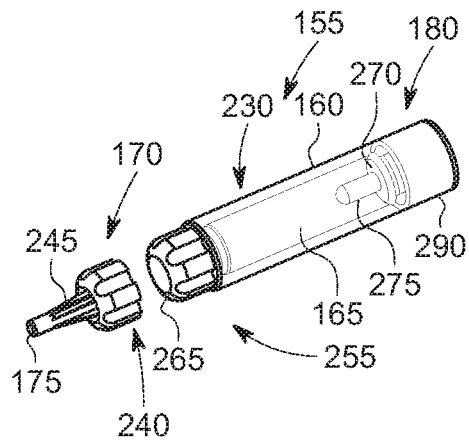
FIG. 2B is a schematic perspective view of the constructed cartridge of FIG. 2A.

A particular version of a cartridge 155 of the dispenser 100 is shown in FIGS. 2A and 2B. In this version, the cartridge 155 is made up of a tube 230 composed of glass, plastic, or metal. The tube 230 makes up the sidewalls 160 of the cartridge 155 and its interior makes up the reservoir 165. At the forward end of the tube 230 are threads 235 for engaging a corresponding threaded section 240 on a replaceable tip 245. The replaceable tip 245 has a conduit 250 extending from the threaded section 240 to the outlet 175. When the replaceable tip 245 is threaded onto the threads 235 of the tube 230, the conduit 250 is in fluid communication with the reservoir 165. After the liquid in the reservoir 165 has been dispensed, the replaceable tip 245 can be removed so the replaceable tip 245 and/or tube 230 can be cleaned and refilled. Alternatively, the replaceable tip 245 can be disposed of and another replaceable tip 245 can be used. The cartridge 155 may optionally also be provided with a cap 255, as shown in FIG. 2A. The cap 255 has a threaded section 260 similar to the threaded section 240 of the replaceable tip 245 so the cap 255 can be threaded onto the tube 230. The cap 255 has a closed front end 265 without an opening. Thus, when installed onto the tube 230, the cap 255 seals the front end of the tube 230 and prevents the escape of liquid in the reservoir 165. FIG. 2B shows the cap 255 installed on the tube 230. In this configuration, the cartridge 155 can be prefilled with liquid and stored for later use. The cap 255 also provides an air tight seal that protects the fluid from oxygen and outside contaminants during storage. When the liquid is to be dispensed, the cap 255 is removed, the replaceable tip 245 is installed, and the cartridge is inserted into the body 105 of the dispenser.

FIGS. 2A and 2B also show a particular version of the plunger 180 of the cartridge 155. In this version, the plunger 180 includes a plunger head 270 that has an outer surface 185 that engages the inner surface of the tube 230. The plunger head 270 of FIGS. 2A and 2B also includes a protruding portion 275 that is sized and shaped to fit within a narrowed portion 280 of the tube 230 near the threads 280. The protruding portion 275 helps to push any liquid in the narrow portion 280 towards the outlet 170 and thereby helps to eliminate wasted liquid. A plunger back portion 285 connects with the plunger head 270 and includes the rear surface 190 that can be contacted by the forward end 205 of the plunger contacting member 200. In an alternative version, the plunger head 275 and the plunger back portion 285 are formed as a single piece. A cover member 290 secures the plunger head 270 and the plunger back portion 285 within the tube 230. The cover member 290 slides over the rear of the tube 230 and a projection 295 on the inner surface of the cover member 290 engages within slot 300 on the tube to attach the cover member 290 to the tube 230. A lip 305 on the rear of the cover member 290 extends a sufficient distance to block the plunger back portion 285 from being able to slide out of the back of the tube 230. An opening 310 in the cover portion 290 provides access to the plunger contacting member 200 and allows it to contact the plunger back portion 285.

Figure 2C:
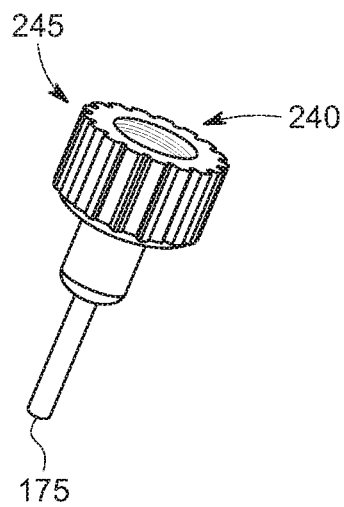
FIG. 2C is a schematic perspective view of a version of a tip of the dispenser of FIG. 1A.

FIG. 2C shows a different replaceable tip 245 of the dispenser 100. In this version, the replaceable tip 245 has a tip and a body made from different materials, such as different metals. For example, in one version, the tip can comprise stainless steel and the body of the tip can comprise brass. This design provides heat resistance from one of the materials and heat dissipation from another material. In this way, the cartridge 155 can be protected against deleterious heat.

In one version of the invention, the dispenser 100 can be provided with multiple and different replaceable tips 245. For example, the replaceable tips 245 can be of different size and/or shapes. The different replaceable tips 245 can be used to produce different sized droplets for a particular liquid. In addition or alternatively, the different replaceable tips 245 can be used to adjust for viscosity of different liquids.

A particular version of the body 110 and the plunger advancement mechanism 195 is shown in FIGS. 3A, 3B, and 3C. FIGS. 3A and 3B show exploded side and sectional views, respectively, and FIG. 3C shows the dispenser of this version 100 assembled. The body 105 in the version of FIGS. 3A and 3B includes a front section 140 and a rear section 145, as discussed above, that are connected at connector 150. In this version, the connector 150 is made up of engageable threads 315 so that the back section 145 can be screwed onto the front section 140. When the front section 140 and the rear section 145 are disconnected, access can be had to the interior 135 of the body 110 and a cartridge 155 (not shown in FIGS. 3A and 3B) can be inserted into the interior 135 of the front portion 305. Then the front section 140 and the rear section 145 can be connected to contain the cartridge 155 within the interior 135. The front section 140 can contain one or more windows 320 that allow a user to visualize the cartridge 155 and its level of fill of liquid.

A plunger contacting member 200 extends within the interior 135 of the rear section 145 of the body 105 and into the front section 140. The plunger contacting member 200 includes a forward end 205 having a surface 325 adapted to contact the rear surface 190 of the plunger 180. The plunger contacting member 200 has a shaft 330 that extends rearwardly from the forward end 210. The shaft 330 includes threads 335 extending along at least a portion of its length. A nut 340 has an interior 345 that receives the shaft 330 of the plunger contacting member 200. The interior 345 of the nut 335 is threaded so that it may threadedly engage the threads 335 on the shaft 330. The nut 340 also includes a polygonal head 350, such as a hexagonal head, to facilitate gripping and rotation of the nut 340.

A shaft capture member 355 includes an opening 360 through which the shaft 330 of the plunger contacting member 205 can slidably pass. The opening 360 is unthreaded and includes one or more flat sides 365 that mate with one or more flat sides 370 on the shaft 330. The flat side 365 of the opening 350 and the flat side 370 of the shaft 330 prevent the shaft 330 and the shaft capture member 355 from rotating relative to one another. The shaft capture member 355 also includes ridges 375 on its outer cylindrical surface. When the dispenser 100 is assembled, as shown in FIG. 3C, the shaft capture member 355 resides within a piece 380 of the rear section 145 of the body 105. On the interior of the piece 380 are longitudinally extending projections 385 that receive the ridges 375 on the shaft capture member 355 to prevent the shaft capture 355 from rotating relative to the piece 380 and the body 105. In another version, the shaft capture member 355 and the piece 380 are formed as a single piece.

As can be seen in FIG. 3A, when the shaft capture 355 is installed on the shaft 330, the shaft 330 is received within the threaded interior 345 of the nut 340, and the shaft capture member 355 is prevented from rotation by the ridges 375, rotation of the nut 340 causes the shaft 330 to advance or retract within the threaded interior 345. Thus, when the nut 340 is prevented from longitudinal movement, rotation of the nut 340 in the advancement direction will cause the shaft 330 to advance within the body 110. A rotational end cap 400 is thus provided to prevent the longitudinal movement of the nut 340. The end cap 400 includes a cylindrical portion 405 that is received within the interior of the piece 380. One or more annular projections 410 are provided on the cylindrical portion 405. The one or more annular projections 410 cooperate with one or more annular projections 415 on the interior of the piece 380 to provide a press-fit attachment. The press-fit attachment of the end cap 400 and the piece 380 allows the end cap 400 to rotate relative to the piece 380 and thus to the rest of the body 110. The end cap 400 is sized so that when installed within the piece 380, a forward end 420 of the end cap 400 contacts the shaft capture member 355 and lightly presses the shaft capture member 355 against a forward wall of the piece 380. The interior of the end cap 400 includes a polygonal portion 425 that matingly receives the polygonal head 350 of the shaft 330. Accordingly, as the end cap 400 is rotated, the nut 340 is also rotated, and the shaft 330 advances or retracts relative to the body 105.

The end cap 420 and the shaft capture 355 also cooperate to make up the metering unit 210 of the dispenser 100. The forward end 420 of the end cap 400 is provided with a plurality of longitudinally extending teeth 430. The shaft capture 355 includes one or more tongues 435 that extend longitudinally towards the end cap 400 and are receivable between adjacent teeth 430 when the end cap 400 contacts the shaft capture 355. As the end cap 400 is rotated in the shaft advancement direction, a tooth 430 compresses the tongue 435 and causes the tongue 435 to move slightly towards the front of the device. When the rotation is enough the tongue 435 travels beyond the apex of the tooth 430, the compression is relieved and the tongue 435 snaps back into a space between adjacent teeth 430. A user receives a tactile and/or an audible feedback when this happens, indicating to the user that a predetermined amount of rotation has occurred. The predetermined rotation results in a predetermined advancement of the plunger contacting member 210 and the plunger 185, and a predetermined or metered amount of the liquid is dispensed through the outlet 175. Thus, the tongue 435 operates as a detent that travels along a tooth 430 and is increasingly biased by the tooth 430 until it reaches the end of the tooth 430 and snaps into a space between adjacent teeth 430.

As also shown in FIGS. 3A, 3B and 3C, the dispenser 100 can include a front cap 450. The front cap includes one or more projections 455 on its interior that can engage one or more projections 460 on the body 105 so the front cap 450 can be press-fit onto the front section 140 of the body 105. In the version shown, the front section 140 can include a reduced diameter portion 465 so the outer profile of the front cap 450 and the body 105 is smooth, as shown in the assembled form in FIG. 3C.

Figure 5A:
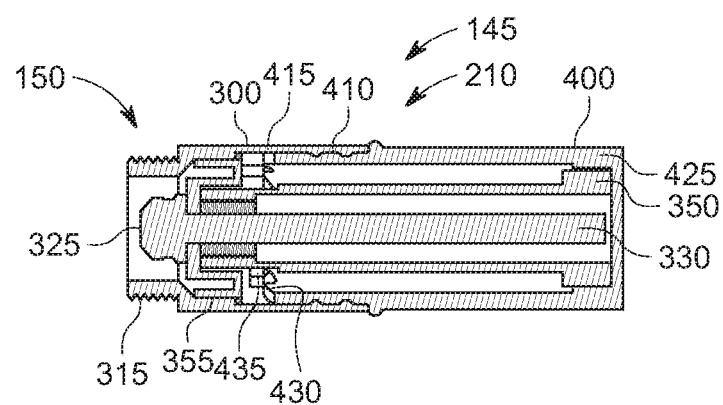
FIG. 5A is a schematic sectional view of the rear section of the dispenser of FIG. 4A.
Figure 5B:
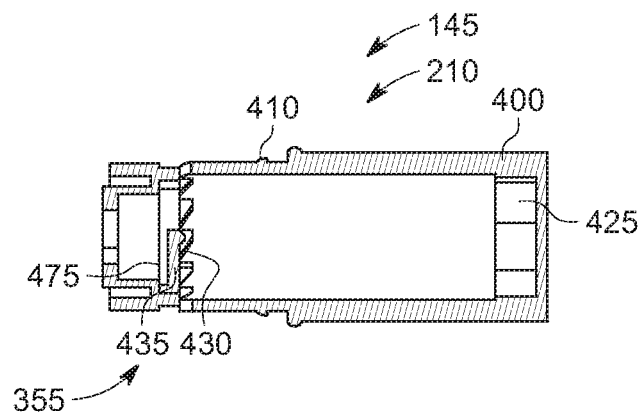
FIG. 5B is a schematic side view of the rear section of the dispenser of FIG. 5A.

FIG. 4A is similar to FIG. 3B but shows the cartridge 155. FIG. 4B is a side cross-section of the assembled dispenser 100 according to this version of the invention. FIGS. 5A and 5B illustrate in more detail the portion of the rear section 145 including the metering unit 210. As can be seen and as has been discussed above, a tooth 430 on the forward end 420 of the end cap 410 engages a tongue 435 on the shaft capture member 355. The tongue 435 is on the end of a cantilever arm 475 of the shaft capture member 355. The cantilever arm 475 allows the tongue 435 to move in a forward direction as the end cap 400 is rotated and the tooth 430 pushes the tongue 435 in the forward direction. When the apex of the tooth 430 passes over the tongue 435, the cantilever arm 475 returns the tongue 435 shown in FIG. 5C.

The metering unit 210 is useful in providing a precisely metered droplet 220 in a reproducible manner, as discussed above. The metering unit 210 is also advantageous in that it provides a feedback to the user that a metered droplet 220 has been produced. As the end cap 410 is rotated, a tooth 430 causes the tongue 435 to move forward against a bias created by the cantilever arm 475. The rotational force required to overcome this bias can be felt and/or heard by the user. Once the apex of the tooth 430 is passed, the tongue 435 snaps back into its unbiased position and this provides a tactile and/or audible feedback to the user. The snap of the tongue 435 can generate an audible sound which provides the audible feedback to the user. Thus, the user can easily know when sufficient rotational force has been applied to produce a droplet.

The liquid dispenser 100 can be used for dispensing various types of liquids for various uses. For example, a metered droplet from the dispenser can be delivered to a vaping tool, such as an electronic cigarette or e-cig that provides access to exposed heating coils for aerosolization of the liquid and administration to a user. Alternatively, the dispenser can dispense a metered droplet that can be taken orally. A droplet can be placed on or under the tongue directly or via an intermediary tool, and/or a droplet can be licked off of the droplet receiver 500 by a user. In another use, a metered droplet can be introduced into another liquid in a cup or container that is to be taken orally by a user. In another version, a metered droplet from the dispenser 100 can be used to provide a metered amount of a liquid component in a formulation. For example, the droplet may contain an active ingredient or excipient that is useful in a pharmaceutical formulation. In another example, the metered droplet can contain a precise amount of an oil and/or an essential for use in a cosmetic or the like. In yet another example, the metered droplet can be used to measure a precise amount of a liquid for a food recipe or other dietary need. In one version, the liquid dispenser 100 is used to administer a pharmaceutically active agent to a user in one or more of the above manners.

In one particular version, the liquid dispenser 100 is used to dispense a droplet of liquid comprising cannabidiol (CBD). CBD is a cannabinoid in *Cannabis*. CBD is believed by many to not have the degree of psychoactive effects associated with some other cannabinoids. CBD is also believed to have many medical uses including, for example, the alleviation of pain associated with multiple sclerosis. CBD is also reported, though not yet medically proven, to be useful in the treatment addiction, inflammation, epilepsy, cancer, and anxiety disorders. Accordingly, in this version of the invention the reservoir 165 of the cartridge 155 is filled with an oil comprising CBD. The liquid dispenser 100 is then used to produce a metered droplet of the oil comprising CBD. In one particular version, a droplet of from about 1.5 µl to about 2.0 µl is produced. The amount of CBD in the oil droplet can be adjusted based on the concentration of CBD in the oil in the reservoir 165 and can depend on the user and treatment.

The dispenser 100 can be designed for a single use or for multiple uses. In a single use version, the cartridge 155 can be prepackaged within the outer body 110. In a multiple use version, the cartridge 155 can be insertable into the outer body 110. In this version, the outer body 110 and the metering unit 210 can be used multiple times with new cartridges 155 inserted. The cartridges 155 can be disposable or refillable.

Although the present invention has been described in considerable detail with regard to certain preferred versions thereof, other versions are possible, and alterations, permutations and equivalents of the version shown will become apparent to those skilled in the art upon a reading of the specification and study of the drawings. For example, the cooperating components may be reversed or provided in additional or fewer number. Also, the various features of the versions herein can be combined in various ways to provide additional versions of the present invention. Furthermore, certain terminology has been used for the purposes of descriptive clarity, and not to limit the present invention. Throughout this specification and any claims appended hereto, unless the context makes it clear otherwise, the term "comprise" and its variations such as "comprises" and "comprising" should be understood to imply the inclusion of a stated element, limitation, or step but not the exclusion of any other elements, limitations, or steps. Therefore, any appended claims should not be limited to the description of the preferred versions contained herein and should include all such alterations, permutations, and equivalents as fall within the true spirit and scope of the present invention.

What is claimed is:

1. A dispenser for dispensing a metered amount of a liquid, the dispenser comprising:
    a body having sidewalls defining a hollow interior and an opening at a forward end of the body;
    a cartridge having a reservoir adapted to contain a liquid and an outlet at the forward end of the cartridge, the cartridge being sized and shaped to be positioned in the hollow interior of the body so that the outlet is aligned with the opening in the body;
    a plunger positionable in the reservoir and slidable within the reservoir; and
    a metering unit comprising a plunger advancement mechanism that can cause the plunger to slide within the reservoir, the metering unit causing the plunger advancement mechanism to advance the plunger a predetermined amount,
    wherein the metering unit is configured to cause advancement the plunger in the reservoir to apply pressure on the liquid in the reservoir and cause a droplet of the liquid to be dispensed through the outlet, and wherein the dispenser produces a droplet of from about 0.5 µl to about 10.0 µl with a droplet to droplet consistency of ±0.2 µl.

2. A dispenser according to claim 1, wherein the metering unit is rotatable and wherein rotation of the metering unit a predetermined amount causes a predetermined translation of the plunger in the reservoir.

3. A dispenser according to claim 2 wherein the metering unit provides a feedback to a user when the predetermined amount of rotation has occurred.

4. A dispenser according to claim 2 wherein the metering unit comprises a plurality of teeth and a tongue that contacts the teeth as rotation occurs.

5. A dispenser according to claim 1 wherein the droplet size is from about 1.0 µl to about 2.5 µl.

6. A dispenser according to claim 1 wherein the droplet size is from about 1.5 µl to about 2 µl.

7. A dispenser according to claim 1 wherein the droplet to droplet consistency is ±0.1 µl.

8. A dispenser according to claim 1 wherein the outlet is located in a replaceable tip of the cartridge.

9. A dispenser according to claim 8 wherein the dispenser comprises a plurality of different sized replaceable tips.

10. A dispenser according to claim 1 wherein the body comprises a front section, a rear section, and a connector that selectively connects the front section and back section and that allows for disconnection of the front section from the rear section to provide access to the hollow interior.

11. A dispenser for dispensing a metered amount of a liquid, the dispenser comprising:
    a body having sidewalls defining a hollow interior and an opening at a forward end of the body;
    a cartridge having a reservoir adapted to contain a liquid and an outlet at the forward end of the cartridge, the cartridge being sized and shaped to be positioned in the hollow interior of the body so that the outlet is aligned with the opening in the body;
    a plunger positionable in the reservoir and slidable within the reservoir; and
    a metering unit comprising a plunger advancement mechanism that can cause the plunger to slide within the reservoir, the metering unit causing the plunger advancement mechanism to advance the plunger a predetermined amount,
    wherein the metering unit is configured to cause advancement the plunger a predetermined distance in the reservoir to apply pressure on the liquid in the reservoir and cause a droplet of the liquid of from about 0.5 µl to about 10.0 µl to be dispensed through the outlet, and wherein the metering unit provides feedback to a user when the plunger has been advanced the predetermined distance.

12. A dispenser according to claim 11, wherein the metering unit is rotatable and wherein rotation of the metering unit a predetermined amount causes the advancement of the plunger the predetermined distance.

13. A dispenser according to claim 11 wherein the feedback is audible or tactile.

14. A dispenser according to claim 11 wherein the metering unit comprises a plurality of teeth and a tongue that contacts the teeth as rotation occurs and wherein the feedback is generated with the tongue advances past a tooth.

15. A dispenser according to claim 11 wherein the outlet is located in a replaceable tip of the cartridge and wherein the dispenser comprises a plurality of different sized replaceable tips.

16. A dispenser according to claim 11 wherein the body comprises a front section, a rear section, and a connector that selectively connects the front section and back section and that allows for disconnection of the front section from the rear section to provide access to the hollow interior.

17. A method of dispensing a droplet of liquid, the method comprising:
    providing a dispenser comprising
        a body having sidewalls defining a hollow interior and an opening at a forward end of the body;
        a cartridge having a reservoir adapted to contain a liquid and an outlet at the forward end of the cartridge, the cartridge being sized and shaped to be positioned in the hollow interior of the body so that the outlet is aligned with the opening in the body;

a plunger positionable in the reservoir and slidable within the reservoir; and a metering unit comprising a plunger advancement mechanism that can cause the plunger to slide within the reservoir, the metering unit causing the plunger advancement mechanism to advance the plunger a predetermined amount;

actuating the metering unit to dispense a discrete, accurate, and reproducible droplet of liquid of from about 0.5 µl to about 10.0 µl from the outlet; and administering the droplet.

18. The method according to claim 17 wherein the droplet is administered by one of more of being directly delivered in droplet form to a user, being delivered to an aerosolization apparatus, and being mixed with another solid or liquid substance.

19. The method according to claim 17 wherein the liquid comprises an oil or an aqueous solution or mixture.

* * * * *